United States Patent [19]

Lorenzana et al.

[11] Patent Number: 4,995,361
[45] Date of Patent: Feb. 26, 1991

[54] DENTAL FLOSS TOOL

[76] Inventors: Moises B. Lorenzana, 601 Lake Hinsdale Dr., Willowbrook, Ill. 60559; Vance A. Lorenzana, 698 Spring Hill Cir., Naperville, Ill. 60540

[21] Appl. No.: 302,602

[22] Filed: Jan. 27, 1989

[51] Int. Cl.⁵ .............................................. A61C 15/00
[52] U.S. Cl. .................................... 132/324; 132/323
[58] Field of Search ....................... 132/323, 324, 325

[56] References Cited

U.S. PATENT DOCUMENTS

| | | | |
|---|---|---|---|
| 1,219,986 | 3/1917 | Muchow | 132/325 |
| 1,306,689 | 6/1919 | Dysart | 132/325 |
| 2,828,754 | 4/1958 | Stewart | 132/323 |
| 3,734,107 | 5/1973 | Thierman | 132/325 |
| 3,766,931 | 10/1973 | Fielder | 132/325 |
| 3,871,393 | 3/1975 | Wharton | 132/325 X |
| 3,927,687 | 12/1975 | Thierman | 132/325 |
| 4,004,599 | 1/1977 | Rosenfeld | 132/325 |
| 4,254,786 | 3/1981 | Won | 132/325 |
| 4,655,234 | 4/1987 | Bowden | 132/325 |
| 4,790,336 | 12/1988 | Kuo | 132/325 |

Primary Examiner—Robert P. Swiatek
Assistant Examiner—Nicholas D. Lucchesi
Attorney, Agent, or Firm—Neil M. Rose

[57] ABSTRACT

A dental floss tool including two simple snap together plastic parts which form a housing for fixedly mounting a reel of dental floss positioned to supply a length of floss to a support structure comprising two flexible slotted arms and a lock for securing the ends of the length of floss to maintain it under tension across the ends of the arms.

15 Claims, 2 Drawing Sheets

DENTAL FLOSS TOOL

BACKGROUND OF THE INVENTION

The invention relates generally to a dental floss tool and more particularly to a dental floss tool which is compact and provides tangle free storage of dental floss therein.

Although a variety of dental floss tools exist in the marketplace, many of them suffer from a number of faults. Typical among them is that they require a great deal of dental floss to be used when employing the tool or that the tool is relatively complicated and expensive to manufacture. Typical among such prior art devices is that disclosed in U. S. Pat. No. 4,004,599 to Rosenfeld which discloses a dental floss holder having a rotatable dental floss reel confined therein from which a length of dental floss may be extracted and extended over a pair of arms for use. One of the problems with such a device is that a rapid pull on the dental floss to unreel it from the spool can lead to jamming within the dental floss holder. In addition, the arms 21 and 22 are not flexible which makes it relatively difficult to tension the dental floss across the gap 26. Also, another problem is that while a button 25 is available on one of the arms 22 to anchor one end of the dental floss, the other end of the dental floss remains relatively free to move being inhibited only by the frictional engagement of the toothed wheel 12.

U.S. Pat. No. 3,378,017 to Stiles discloses a relatively complicated dental floss device which has been embodied in a commercial device. In that device a number of moving parts are employed and tension is maintained on the dental floss by trapping it between a pair of movable sections of the dental floss applicator. The device would appear to be quite expensive to manufacture.

U.S. Pat. No. 1,171,177 to De L'Eau discloses a dental floss holder having a fixed supply of floss arranged in a coil 22. However, the device is quite complicated to manufacture as the moveable arms 11 and 12 are pivoted at a hinge mechanism 10.

What is needed then is a dental floss tool or holder which is economical, easy to use and provides firm anchoring of the dental floss during use.

SUMMARY OF THE INVENTION

A dental floss tool is disclosed herein having a flattened cylindrically shaped floss storage housing with a spool of dental floss contained therein. The spool of dental floss is held fixed within the storage housing and has its central access aligned perpendicular to a flattened top and bottom of the housing. An aperture is formed in the center of the top of the housing through which dental floss may be removed. A pair of flexible arms are attached to a circular side wall of the housing opposite the fork. A lock button is formed integrally with the housing and defines a tapered circular groove with the cylindrical side wall thereof which comprises the floss lock.

It is a principal object of the present invention to provide a dental floss tool from which stored dental floss may be withdrawn without jamming or tangling.

It is another object of the present invention to provide a dental floss tool which allows the user to lock securely both ends of a length of dental floss to provide adequate tensioning thereto.

It is another object of the instant invention to provide a dental floss tool which is compact, economical and easy to use.

Other objects and advantages of the present invention will become obvious to one skilled in the art upon a perusal of the specification and claims in the light of the accompanying drawings

DESCRIPTION OF THE PREFERRED EMBODIMENT

Figure 1:
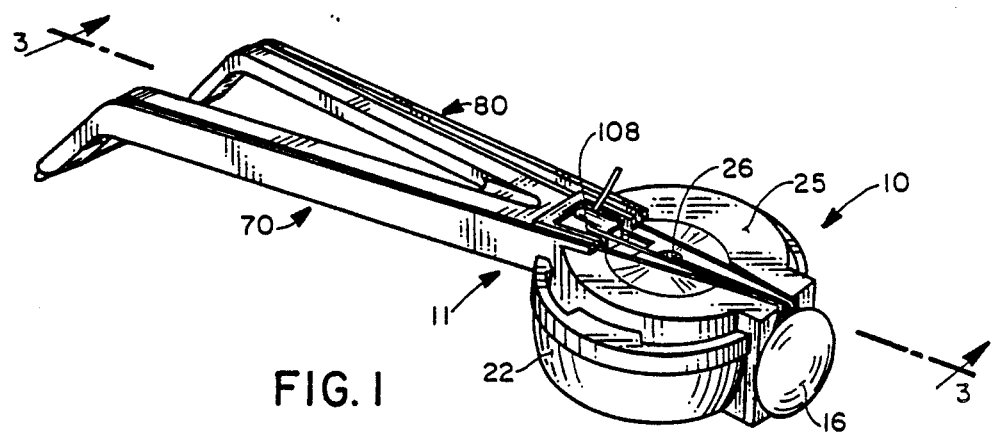
FIG. 1 is a perspective view of a dental floss tool embodying the present invention showing details of the manner in which a length of dental floss is extended in operative engagement about the various portions of the tool.
Figure 2:
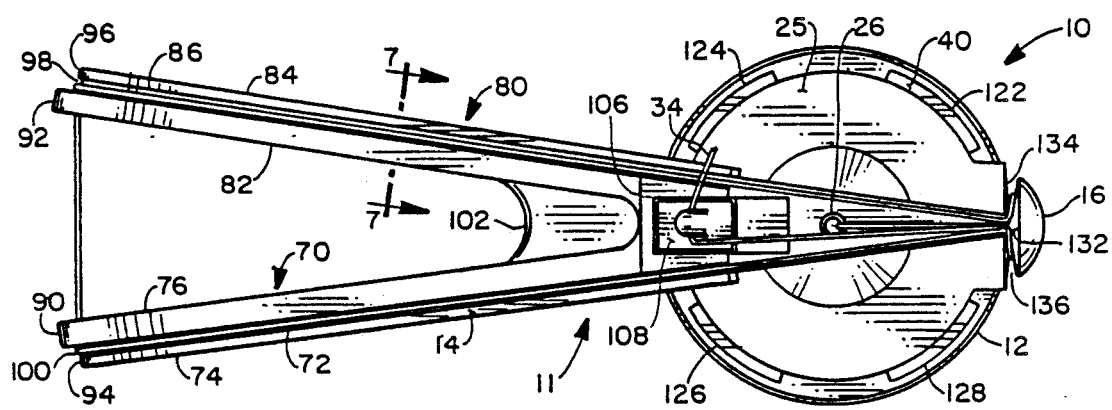
FIG. 2 is a top plan view of the dental floss tool showing details of the cutter, the arms and the lock button.

Referring now to the drawings and especially to FIG. 1, a dental floss tool embodying the present invention and generally identified by numeral 10 is shown therein. The dental floss tool 10 includes a floss storage housing or container 12 having a fork 14 formed integrally therewith. A lock means or button 16 is mounted on the side of the housing 12.

The floss storage housing 12 is a substantially right circular cylindrical housing consisting of a circular bottom wall 20 having a rounded, tapering, generally cylindrical side wall 22 formed integrally therewith. A cross shaped spool holding shaft 24 is formed integrally with the bottom wall 20 and is adapted to receive a spool of floss 30. A top cap 25 forms a top wall of the housing 12 and has an aperture 26 formed therein. The aperture 26 is positioned centrally over the spool holding shaft 24.

The floss tool 10 is made up of two simple molded plastic parts, the first being a fork assembly 11 which includes the fork 14 and the top cap 25 of the floss storage housing 12 and the second being a cup assembly 13 which includes the bottom wall 20 and the side wall 22. As will be explained in detail below, these two parts, the fork assembly 11 and the cup assembly 13 snap fit together to form the storage container for the floss and the means for conveniently supporting increments of the floss for use in cleaning the teeth.

The spool of dental floss 30 comprising a spool body 31 and a quantity of dental floss 32 is force fitted over the spool holding shaft 24 and is thus fixed against rotation with respect to the housing 12. A floss starting end 34 is withdrawn from the length of floss 32 through the aperture 26.

Figure 9:
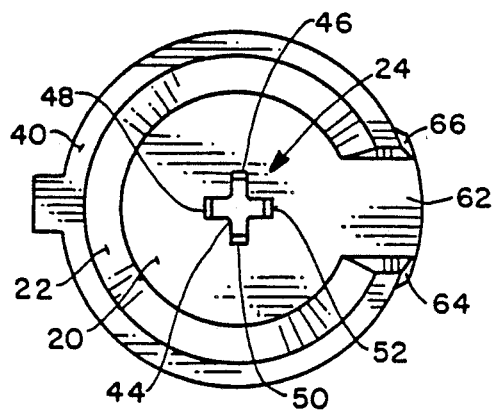
FIG. 9 is a top plan view of the cup assembly portion of the floss storage housing.
Figure 10:
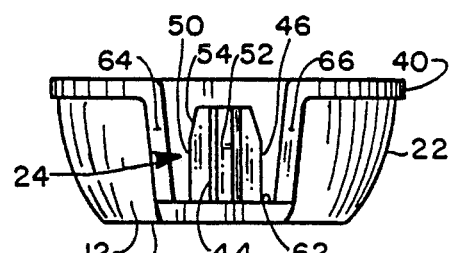
FIG. 10 is an elevational view of the cup assembly.
Figure 11:
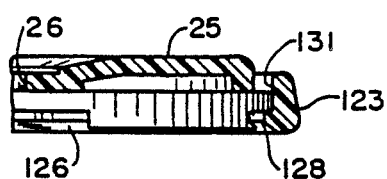
FIG. 11 is an enlarged sectional view taken on line 11—11 of FIG. 6.

The bottom wall 20 and the side wall 22 of the floss housing 12 are molded as the unitary cup assembly 13 from high density polypropylene. The side wall 22 terminates in an outwardly extending flange or lip 40 which is adapted to engage other portions of the dental floss tool 10 in locking engagement. The spool shaft 24 consists of a shaft having a circular central section 44 formed integrally with the bottom wall 20 and extending perpendicularly therefrom. A plurality of vanes respectively numbered 46, 48, 50 and 52 as shown in FIG. 9 extend from the central shaft 44 and are spaced at 90 degree intervals about the central shaft 44. The upper portions of the vanes are slightly tapered at their upper ends as shown at 54 on the vanes in FIG. 10 in order to facilitate the assembly of the floss spool to the shaft 24. The vanes are at such a distance from the axis of shaft 24 that they cause the spool of floss 30 to deform slightly as it is forced onto the shaft 24 so that the spool body 31 is securely attached to the shaft 24.

Figure 3:
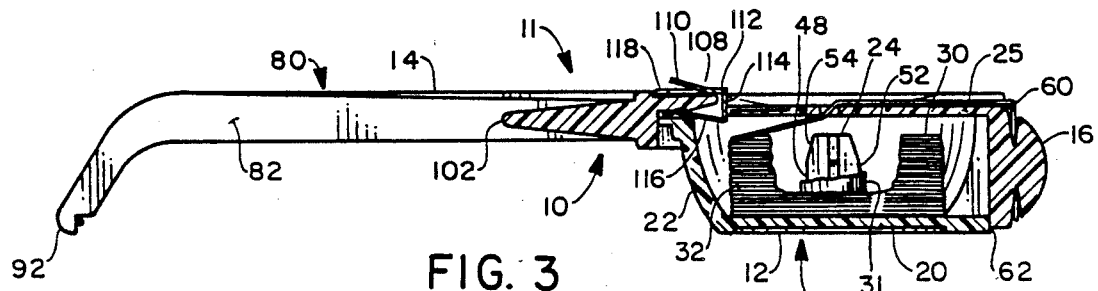
FIG. 3 is a sectional view taken substantially along line 3—3 of FIG. 1 showing details of the internal structure of a spool holding assembly and a lock button attached to the assembly.
Figure 4:
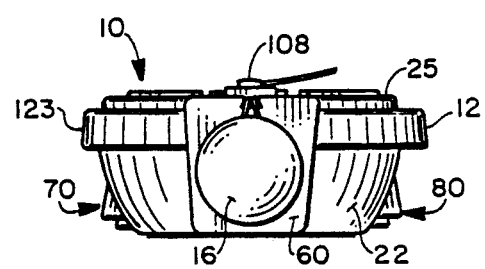
FIG. 4 is an end elevational view of the dental floss tool of FIG. 1 showing the arrangement of the lock button and its mounting on the fork assembly.
Figure 5:
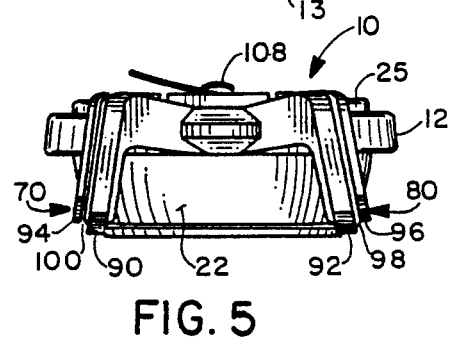
FIG. 5 is another end elevational view of the dental floss tool showing details of the flexible arms.

The lock means 16 is an integral part of the fork assembly 11 and is mounted on a support 60 which extends downwardly from one edge of the cap 25 as shown in FIG. 3. The support 60 is received in a cut out or opening 62 in the side wall 22 of the cup assembly 13. The opening 62 is defined by reinforcing walls on the cup assembly 13 including a first reinforcing upright vane 64 and a second reinforcing upright vane 66 both being formed integrally with the cup assembly 13.

Figure 7:
FIG. 7 is an enlarged sectional view of one of the arms taken on line 7—7 of FIG. 2.

The top cap 25, the locking means 16, the support 60 and the fork 14 comprise the fork assembly 11 which is composed of ABS plastic. The fork assembly 11 includes a first flexible arm 70 extending substantially coplanar with the top cap 25, The first flexible arm 70 is substantially rectangular in cross-section and defines a groove 72 on an upper surface thereof for guiding a length of dental floss therealong. The groove 72 is defined by an outer member 74 and an inner member 76. Likewise, a second flexible arm 80 has an inner member 82, an outer member 84 and a groove 86 defined thereon. As best shown in the enlarged sectional view of FIG. 7, the outer member 84 extends higher above the groove 86 than does the inner member 82 so as to facilitate the user's insertion of the floss into the groove 86. Similarly, the outer member 74 on the arm 70 extends higher above the groove 72 than does the inner member 76.

At the unsupported ends of the arms 70 and 80, the inner members 76 and 82 extend slightly past the outer members 74 and 86 to terminate, respectively, at an ear 90 formed integrally with the inner member 76 and an ear 92 formed integrally with the inner member 82. Immediately adjacent the ears 90 and 92 are, respectively, a second ear member 84 adjacent ear member 90 and a second ear member 96 adjacent ear member 92, Ear members 92 and 96 define a floss entrapment slot 98. Ear members 90 and 94 define a floss entrapment slot 100. In order to provide additional strength for the flexible arms 70 and 80, there is provided a curved web assembly 102 formed integrally therebetween.

Figure 6:
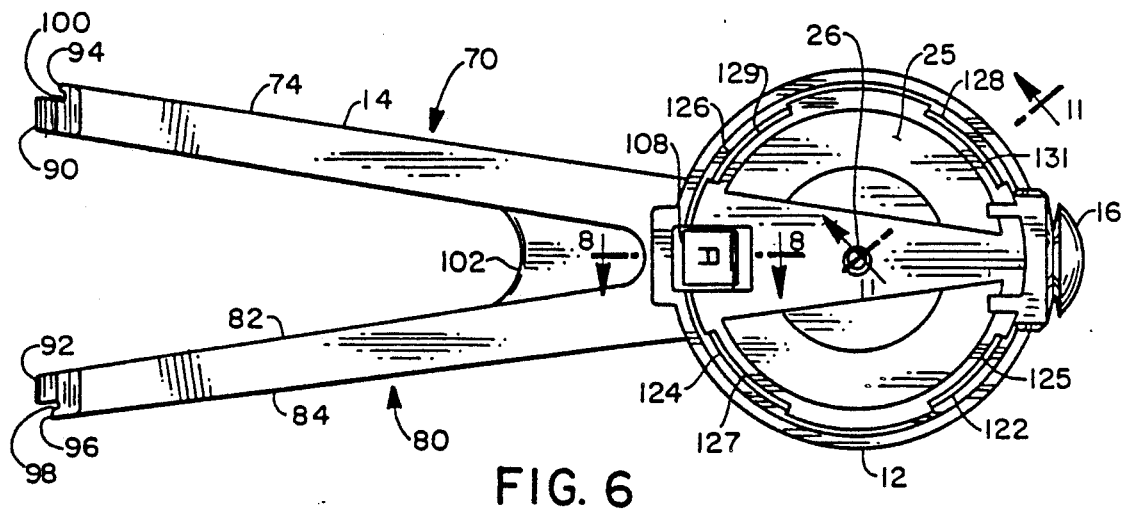
FIG. 6 is a bottom plan view of the fork assembly portion of the tool, the spool and spool holding assembly being removed.

The arms 70 and 80 terminate in an apex portion 106. Adjacent the apex portion 106 there is supported on the fork assembly 11 a metal floss cutter assembly 108 which is a generally U-shaped clip adapted to snap into assembled relation with the fork assembly 11. The metal floss cutter 108 is composed of 310 or 410 stainless steel having a thickness of 0.010 to 0.012 inches. The stainless steel is spring tempered. The cutter 108 consists of a rounded tongue 110 formed integrally with a horizontal base 112. A vertical wall 114 is formed integrally with the horizontal base 112 and a spring leg 116 is formed integrally with the wall 114 extending generally parallel to the base 112. The cutter assembly 108 extends through an opening 119 in the cap 25 and is positioned adjacent to the aperture 26 as may be seen in FIG. 6.

Figure 8:
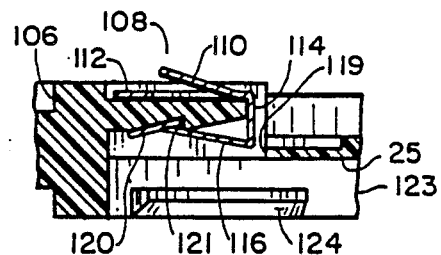
FIG. 8 is an enlarged sectional view of the floss cutter taken on line 8—8 of FIG. 6.

The spring leg 116 is formed with a locking tab or barb 120 which extends from the leg 116 upwardly toward the base 112. The locking tab 120 engages a recess in the lower surface of the cap 25. The recess includes a vertical wall 121 against which the locking tab 120 engages to prevent the cutter assembly 108 from being withdrawn to the right from the assembled positioned as shown in FIG. 8. It should be understood that the cutter assembly 108 is sufficiently resilient to permit the base 112 and the leg 116 to be separated during assembly after which the locking tab 120 seats in the recess against the wall 121 to retain the cutter assembly 108 rigidly secured to the cap 25 and the fork assembly 11.

The top cap 25 includes a plurality of tapered shoulders 122, 124, 126 and 128 which are adapted to engage in a snap fit relationship the lip 40 of the cup assembly 13. The tapered shoulders are supported on a downwardly extending peripheral flange 123 on the cap 25. Above each of the four shoulders 122, 124, 126 and 128 there are provided slots 125, 127, 129 and 131 which facilitate the molding of the fork assembly 11. The tapered shoulders are angled inwardly or beveled from the bottom upwardly so that as the cup assembly 13 is assembled to the bottom of the fork assembly 11, the wall 22 and the lip 40 of the cup assembly deflect inwardly as the cup rim or lip 40 passes over the tapered shoulders until the lip 40 snaps into position over the top of the shoulders which retain the cup assembly 13 assembled against the bottom of the cap 25. In such assembled position, the opening 62 in the wall 22 of the cup assembly is closed by the support 60 which engages the reinforcing vanes 64 and 66 in the side wall 22 providing added support for the cup assembly 13.

The lock means 16 includes a button 130 having a tapered or conical interior face 132. The tapered interior face 132 is in close proximity with an oppositely tapered face 134 forming a back portion of the support 60 to thereby define a locking groove 136 which is adapted to receive a quantity of dental floss therein. The conical faces 132 and 134 intersect at a sharp angle forming a very thin slot into which the floss 32 may be forced to lock it against displacement.

The dental floss spool 30 holds 50 yards of waxed or unwaxed nylon dental floss 32 and is commercially available from Belding Corticelli Thread Company of Charlotte, N.C. or other well known suppliers.

In order to assemble the dental floss tool 10, the molded cup assembly 13 receives the dental floss spool 30 over the shaft 24 in press fitted engagement. The fork assembly 11 is brought into proximity with the floss 32 and a length of floss 34 is drawn through the aperture 26. The top cap 25 is then snap fitted over the cup rim 40 for secure engagement therewith. Finally, the spring leg 116 of the cutter assembly 108 is slid through the opening 119 in the top cap 25 and into assembled engagement with the fork assembly 11 as shown in FIG. 3 to complete the assembly of the tool 10.

In use, an 18 inch length of floss 34 is initially withdrawn from the aperture 26 and the portion adjacent aperture 26 is secured by wrapping it once around the lock means 16 in the groove 136 whereby it is securely entrapped. The floss is then run along the groove 72, through the slot 100, past the ear 90, across to the arm 80, past the ear 92, through the slot 98, back down the groove 86 to the locking means 16 where the floss 34 is again wrapped two times around the locking means 16 in the groove 136. While the floss is thus being secured, the arms 70 and 80 are bent inwardly toward each other so as to be approximately ¾" apart at their free ends. Thus, in order to make sure that the floss 34 is adequately tensioned for use, while the floss is being threaded along the arms 70 and 80, the arms 70 and 80 are squeezed together slightly taking advantage of their flexible nature. When the floss 34 has been secured at both ends, the arms 70 and 80 are released, thereby drawing the length of floss 34 taut between the arms 70 and 80. After the dental floss tool 10 has been used, if it is desired to reuse it, it is first necessary to unlock the ends of the floss 34 from the locking means 16 to permit the user to withdraw an additional 8" of floss from the storage housing 12 through the aperture 26. The floss is then locked again to the lock means 16 engaging first the attached end into the groove 134 and then inserting the floss into the grooves 72 and 86 as described above. The other end of the floss is then secured in the lock means 16 and the used portion of the floss, about 8" is cut off in the cutter assembly 108.

Thus, it may be appreciated that an economical dental floss tool 10 is herein disclosed which uses very little dental floss and is very compact. The dental floss tool 10 also provides positive securing of both ends of a length of dental floss 34 to prevent it from loosening while the floss is in the user's mouth. The structure of the arms 70 and 80 with their grooves 72 and 86 provides an improved means for protecting the floss that is not actually engaged with the teeth and protecting the portions of mouth from engaging the floss.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

What is claimed and is desired to be secured by Letters Patent is;

1. A dental floss, comprising:
a floss housing having a fixed spool of dental floss located therein, said fixed spool of dental floss being symmetric about a spool axis, said floss housing having an aperture formed in said floss housing in substantial alignment with said spool axis for withdrawal of a quantity of dental floss from said housing;
a fork attached to said housing having a first arm and a second arm, said first arm having a first arm portion extending from said housing substantially at a right angle to said spool axis, said second arm having a second arm portion extending from said housing substantially at a right angle with respect to said spool axis, said first and second arms each being formed with a lengthwise extending groove from said housing to an end remote from said housing, and a dental floss lock means mounted on said the other opposite said fork for locking both ends of a length of floss, extending the entire length of said first and second arms within said grooves and extending and between said remote ends of said first and second arms, said lock means being substantially aligned with said grooves in said first and second arms, said first and second arm portions being at an acute angle to each other and being readily flexed to tension the dental floss extending between said first and second arms, said lock means being positioned to permit securing of the free end of a length of floss one end of which is already secured to said lock means so that the resilience of said arm portions will maintain said length of floss under tension with both ends secured to said lock means.

2. A dental floss tool comprising:
a fork assembly, having a circular disc-like cap which is coplanar with a pair of flexible arms, said cap having a circular edge from which said arms extend at an acute angle to each other to form a floss supporting yoke, a cup shaped floss container being generally cylindrical with a central axis and a bottom from which a support post for a floss reel extends, a floss reel received on said post in an interference fit to fixedly secure said reel with respect to said container, interengaging lips and shoulders on said container and said cap to retain said container to said fork assembly with said cap and said container forming an enclosure for said floss, an opening in the center of said cap to permit unreeling of said floss from the container into engagement with said yoke, locking means on said cap aligned with each of said flexible arms to secure opposite ends of a length of floss which extends lengthwise of each of said arms with a short exposed length of floss being tensioned between the ends of said arms remote from said cap, said flexible arms each being formed with a groove extending lengthwise from said cap to said remote end to receive a length of floss extending from said locking means to said remote end, said flexible arms being readily deflected to move said ends of said arms remote from said cap Closer together to apply tension to said length of floss, the ends of which are secured to said locking means, said locking means being positioned to permit securing of the free end of a length of floss, the other end of which is already secured to said locking means, so that the resilience of said flexible arms maintains said length of floss under tension with both ends secured to said locking means.

3. The combination of claim 2 wherein said cap is formed with a second opening to receive a floss cutter, said floss cutter comprising a U-shaped clip having a cutting blade formed in a leg of said U-shaped clip and a retaining portion formed by another leg of said clip, said clip extending through said second opening with said cutting blade extending on one side of said cap and said retaining portion engaging the other side of said cap within said enclosure to secure said clip with respect to said cap.

4. The combination of claim 2 wherein said arms are each formed with a notch formed on each of said ends remote from said cap to support said length of floss extending between said ends remote from said cap.

5. The combination of claim 4 wherein said locking means is located on said container at the intersection of the extension of said grooves formed on said arms.

6. The combination of claim 5 wherein said locking means comprises a button mounted on said cap and forming with said cap a narrow groove around which floss may be wound to secure both ends of a length of floss under tension.

7. A dental floss tool comprising;
a floss storage housing which is cylindrical in shape, said housing being formed with means for fixedly supporting a reel of dental floss wound about a central axis, said housing having a floss outlet aperture located on said central axis, a pair of support arms extending radially from one side of said housing at an acute angle to each other, each arm having a main portion attached to said housing and an angled end portion joined to said main portion and having an outer end which is displaced from said main portion and formed with notches to support an operating length of floss between said outer ends, said arms having lengthwise extending grooves running from said housing to said outer ends to receive dental floss to tension said operating length, the portions of said grooves in said main portion of said arm being in substantially the same plane as said floss outlet aperture, floss locking means supported on said housing on the side of said housing opposite from the side to which said arms are attached, said floss locking means being aligned with said grooves whereby a length of floss may be secured at its ends to said locking means and extend through said grooves and notches to support said operating length under tension, said support arms being flexible to permit deflection of said angled end portions toward each other to apply tension to said length of floss secured to said locking means, said locking means being positioned to permit the securing of the free end of a length of floss the other end of which is already secured to said locking means so that the resilience of said flexible arms maintains said length of floss under tension with both ends secured to said locking means.

8. The dental floss tool of claim 7 wherein said arms are formed with coplanar upper surfaces with said grooves being formed along one edge of each of said surfaces, each of said arms having a raised rib defining the edge of said groove remote from each said surface, each said rib extending above its adjacent surface of said arm to facilitate the insertion of a length of floss into said grooves.

9. The dental floss tool of claim 7 wherein said locking means comprises a button mounted on said housing, said button having a conical surface facing said housing and intersecting said housing at an acute angle to provide surfaces which engage and secure dental floss wrapped around said button.

10. The dental floss tool of claim 9 wherein said button and said conical surface have an axis located on the intersection of two vertical planes through said grooves in said arms.

11. The dental floss tool of claim 7 wherein said housing is formed by a cup shaped member having a cylindrical side wall and a bottom wall from which said floss reel supporting means extends, said housing having a circular cover which supports said cup shaped member and forms with said cup shaped member an enclosure for said floss reel, said arms and said circular cover being an integrally molded plastic part, said arms being flexible to maintain tension on said operating length of floss.

12. The dental floss tool of claim 11 including a cutter assembly supported on said cover, said cutter assembly including a U-shaped clip having two parallel spaced legs which engage opposite sides of said cover to secure said assembly thereon, said cutter assembly being positioned between said grooves adjacent the point where said arms extend from said housing.

13. The dental floss tool of claim 11 wherein said cup shaped member and said cover are formed with interengaging lips and shoulders which snap into locking position to secure said cover to said cup shaped member to form said enclosure.

14. The dental floss tool of claim 13 wherein said cup shaped member is formed with a peripherally extending flange at the top of said side wall defining a lip, a plurality of locking shoulders extending from the periphery of said cover to snap beneath said lip and secure said cup shaped member against said cover.

15. The dental floss tool of claim 7 including a cutter assembly secured to said housing, said cutter assembly being a resilient U-shaped clip having two generally parallel legs and an interconnecting portion, said housing being formed with a slot through which said clip extends with one leg within said housing and one leg outside of said housing, said legs gripping said housing to maintain said cutter assembly attached thereto, a cutter blade formed integrally with said leg positioned outside of said housing and adapted to sever a length of dental floss drawn across said blade.

* * * * *